United States Patent
Best et al.

(10) Patent No.: US 12,201,306 B2
(45) Date of Patent: Jan. 21, 2025

(54) SURGICAL IMPACT DRIVER ADAPTORS FOR APPLYING DIRECTED TORQUE AND LINEAR IMPACT LOADS DURING SURGICAL PROCEDURES

(71) Applicant: ARTHREX, INC., Naples, FL (US)

(72) Inventors: Joshua Best, Naples, FL (US); Michael Charles Morris, Naples, FL (US); Kenneth T. Helenbolt, Naples, FL (US); Timothy McIntyre, Naples, FL (US)

(73) Assignee: ARTHREX, INC., Naples, FL (US)

( * ) Notice: Subject to any disclaimer, the term of this patent is extended or adjusted under 35 U.S.C. 154(b) by 207 days.

(21) Appl. No.: 17/669,684

(22) Filed: Feb. 11, 2022

(65) Prior Publication Data

US 2023/0255645 A1 Aug. 17, 2023

(51) Int. Cl.
*A61B 17/04* (2006.01)
*A61B 17/16* (2006.01)
(Continued)

(52) U.S. Cl.
CPC ........ *A61B 17/1633* (2013.01); *B25B 21/007* (2013.01); *B25B 21/02* (2013.01);
(Continued)

(58) Field of Classification Search
CPC . A61B 17/04; A61B 17/1631; A61B 17/1695; A61B 17/1626; A61B 17/8875; A61B 2017/07214; A61B 2017/00473; A61B 2017/00477; A61B 17/1624; B23B 23/00; B25B 21/02; B25B 21/008; B25B 23/14; B25B 23/141; B25B 23/1427; B25B 23/0035; B25B 13/466; B25B 21/00; B25B 21/007; B25B 23/00
(Continued)

(56) References Cited

U.S. PATENT DOCUMENTS 2,683,511 A * 7/1954 McHugh ............. B25B 23/0035
192/56.62
4,362,161 A * 12/1982 Reimels ............. A61B 17/1695
408/139
(Continued)

FOREIGN PATENT DOCUMENTS

BE 498191 A 12/1950
KR 101515883 B1 5/2015
WO 2015146734 A1 10/2015

OTHER PUBLICATIONS

Extended European Search Report for Application No. EP 23 15 6014.5 dated Jun. 12, 2023.

*Primary Examiner* — Scott A Smith
(74) *Attorney, Agent, or Firm* — Carlson, Gaskey & Olds, P.C.

(57) ABSTRACT

Surgical impact driver adaptors may be connected between a powered surgical instrument and a driven surgical device when performing surgical procedures, such as those involving the implantation of a surgical implant into bone, for example. During surgical procedures, the surgical impact driver adaptors may limit a transfer of a rotational force from the powered surgical instrument to the surgical device until a sufficient axial force is applied to the impact driver adaptor from the powered surgical instrument.

20 Claims, 10 Drawing Sheets

(51) Int. Cl.
*B23B 21/00* (2006.01)
*B25B 21/00* (2006.01)
*B25B 21/02* (2006.01)
*B25B 23/00* (2006.01)
*A61B 17/00* (2006.01)
*A61B 17/88* (2006.01)
*A61B 90/00* (2016.01)
*B23B 23/00* (2006.01)
*B25B 13/46* (2006.01)
*B25B 23/14* (2006.01)

(52) U.S. Cl.
CPC ........ B25B 21/026 (2013.01); B25B 23/0035 (2013.01); *A61B 2017/00486* (2013.01); *A61B 17/1624* (2013.01); *A61B 17/1626* (2013.01); *A61B 17/1628* (2013.01); *A61B 17/8875* (2013.01); *A61B 2090/031* (2016.02); *B23B 23/00* (2013.01); *B25B 13/466* (2013.01); *B25B 23/141* (2013.01)

(58) Field of Classification Search
USPC ......... 227/19, 175.1; 173/93, 93.5, 93.6, 96, 173/97, 109, 110, 121, 122, 124, 205
See application file for complete search history.

(56) References Cited

U.S. PATENT DOCUMENTS

| | | | |
|---|---|---|---|
| 5,330,480 A * | 7/1994 | Meloul | A61B 17/1695 606/80 |
| 8,961,358 B2 | 2/2015 | Hirabayashi | |
| 11,097,404 B2 | 8/2021 | Farmer | |
| 2006/0016300 A1 | 1/2006 | Bubel | |
| 2006/0254786 A1 | 11/2006 | Murakami et al. | |
| 2007/0260257 A1* | 11/2007 | Phan | A61B 17/8875 606/84 |
| 2009/0024129 A1* | 1/2009 | Gordon | A61B 17/1617 606/180 |
| 2009/0293687 A1* | 12/2009 | Nino | B25B 23/1427 81/476 |
| 2013/0048460 A1 | 2/2013 | Keller et al. | |
| 2013/0152746 A1* | 6/2013 | Kerboul | B25B 23/1427 81/475 |
| 2013/0161042 A1 | 6/2013 | Blum et al. | |
| 2013/0171585 A1* | 7/2013 | Huang | A61C 8/0092 433/173 |
| 2017/0027594 A1 | 2/2017 | Ujvari | |
| 2021/0219997 A1 | 7/2021 | Tyndall et al. | |
| 2021/0291329 A1 | 9/2021 | Straub et al. | |
| 2021/0362309 A1 | 11/2021 | Cera | |

* cited by examiner

SURGICAL IMPACT DRIVER ADAPTORS FOR APPLYING DIRECTED TORQUE AND LINEAR IMPACT LOADS DURING SURGICAL PROCEDURES

BACKGROUND

This disclosure relates to the field of surgery, and more particularly to surgical impact driver adaptors for use when performing various surgical procedures.

Some surgical procedures require implanting one or more suture anchors within bone. Multiple surgical tools are typically required to prepare a bone hole and insert a suture anchor into the bone hole for suture anchors that require impaction loads.

SUMMARY

This disclosure is directed to impact driver adaptors that may be connected between a powered surgical instrument and a driven surgical device when performing surgical procedures, such as those involving the implantation of a surgical implant into bone, for example.

An exemplary surgical impact driver adaptor may include, inter alia, a first connector adapted to receive a rotational force, a second connector, and an outer locking sleeve that includes a proximal end portion configured to interface with a boss of the first connector and a distal end portion configured to interface with the second connector. An anvil coupling includes a proximal end portion received within an inner bore of the boss of the first connector. The anvil coupling is substantially housed within the boss and the outer locking sleeve. The boss of the first connector provides a hammer feature, and the proximal end portion of the anvil coupling provides an anvil feature that is configured to mate with and engage the hammer feature. A disengagement spring is configured to bias the anvil feature and the hammer feature apart, thereby disengaging the second connector from receiving the rotational force until an axial force that exceeds a predefined threshold is applied to the first connector.

Another exemplary surgical impact driver adaptor may include, inter alia, a first connector adapted to receive a rotational force, a rotational component operably coupled to the first connector, and an engagement assembly configured to disengage the rotational component from receiving the rotational force until an axial force that exceeds a predefined threshold is applied to the first connector.

An exemplary surgical method may include, inter alia, limiting a transfer of a rotational force from a powered surgical instrument to a surgical device until a sufficient axial force is applied to an impact driver adaptor from the powered surgical instrument during a surgical procedure.

DETAILED DESCRIPTION

Figure 1:
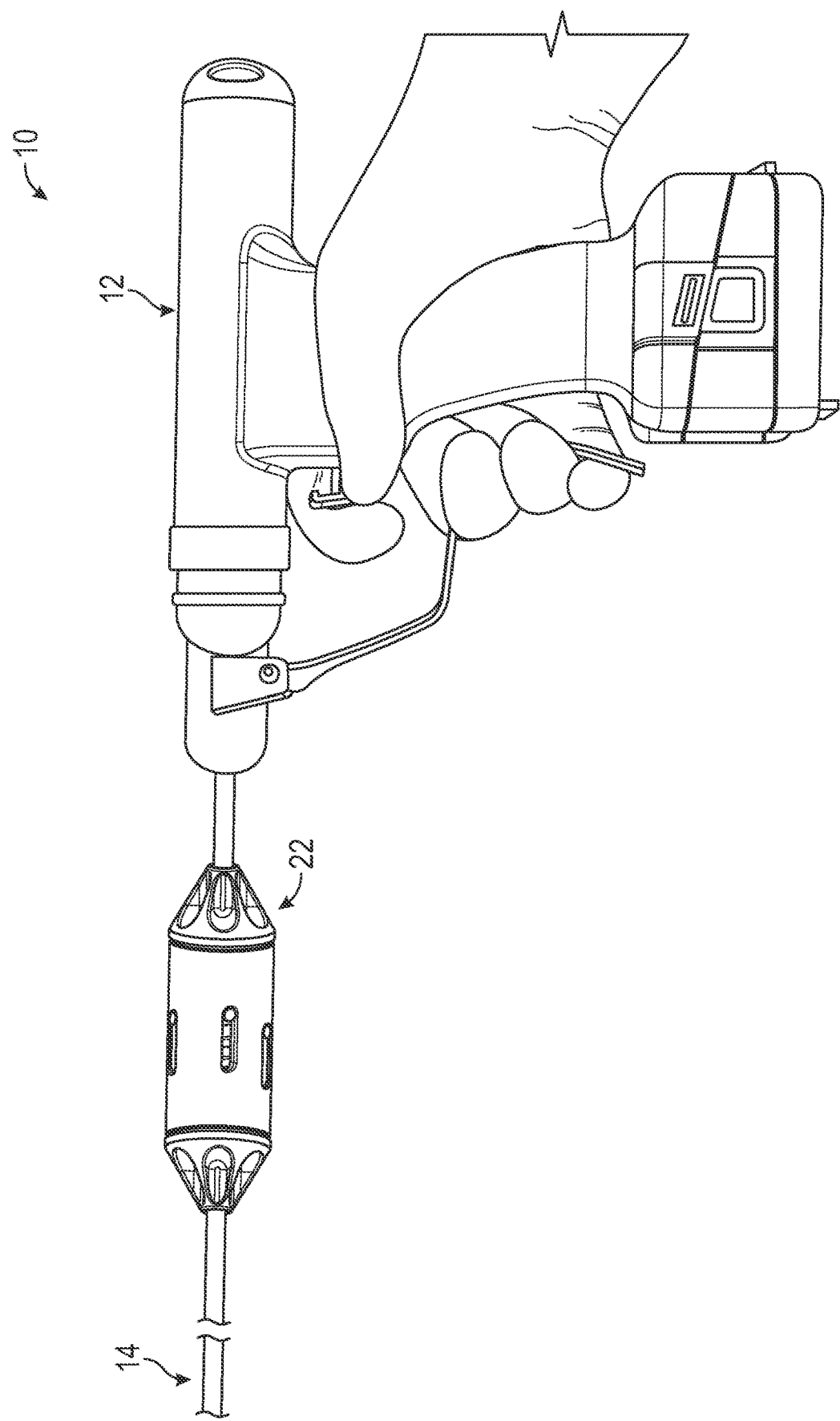
FIG. 1 illustrates an exemplary surgical system for performing surgical procedures.

This disclosure is directed to surgical impact driver adaptors that may be connected between a powered surgical instrument and a driven surgical device when performing surgical procedures, such as those involving the implantation of a surgical implant into bone, for example. During surgical procedures, the surgical impact driver adaptors may limit a transfer of a rotational force from the powered surgical instrument to the surgical device until a sufficient axial force is applied to the impact driver adaptor from the powered surgical instrument. These and other features of this disclosure are described in further detail below.

An exemplary surgical impact driver adaptor may include, inter alia, a first connector adapted to receive a rotational force, a second connector, and an outer locking sleeve that includes a proximal end portion configured to interface with a boss of the first connector and a distal end portion configured to interface with the second connector. An anvil coupling includes a proximal end portion received within an inner bore of the boss of the first connector. The anvil coupling is substantially housed within the boss and the outer locking sleeve. The boss of the first connector provides a hammer feature, and the proximal end portion of the anvil coupling provides an anvil feature that is configured to mate with and engage the hammer feature. A disengagement spring is configured to bias the anvil feature and the hammer feature apart, thereby disengaging the second connector from receiving the rotational force until an axial force that exceeds a predefined threshold is applied to the first connector Another exemplary impact driver adaptor may include, inter alia, a first connector adapted to receive a rotational force, a rotational component operably coupled to the first connector, and an engagement assembly configured to disengage the rotational component from receiving the rotational force until an axial force that exceeds a predefined threshold is applied to the first connector.

In a further embodiment, a first connector of a surgical impact driver adaptor is configured to receive a rotational force from a powered surgical instrument.

In a further embodiment, a rotational component of a surgical impact driver adaptor is configured to connect to a surgical device.

In a further embodiment, a rotational component of a surgical impact drive adaptor is a drive shaft.

In a further embodiment, a rotational component of a surgical impact driver adaptor is a second connector.

In a further embodiment, an engagement assembly of a surgical impact driver adaptor includes a rear clutch cylinder, a front clutch cylinder, and a disengagement spring that is configured to bias the rear clutch cylinder and the front clutch cylinder apart until an axial force exceeds a predefined threshold.

In a further embodiment, a rear clutch cylinder includes a first set of teeth that are configured to engage and mesh with a second set of teeth of a front clutch cylinder.

In a further embodiment, a ramp is established at each location where a first set of teeth engage a second set of teeth.

In a further embodiment, a rotational component of a surgical impact driver adaptor is a drive shaft that is fixedly secured to a front clutch cylinder and free to rotate relative to a rear clutch cylinder.

In a further embodiment, a spring is arranged between a cap of a first connector and a rear clutch cylinder of a surgical impact driver adaptor. The spring is configured to dampen linear impact loads created by an axial force.

In a further embodiment, an engagement assembly of a surgical impact driver adaptor includes a hammer feature provided by a first connector, an anvil feature provided by an anvil coupling, and a disengagement spring that is configured to bias the hammer feature and the anvil feature apart until an axial force exceeds a predefined threshold.

In a further embodiment, a hammer feature includes a first set of teeth that are configured to engage and mesh with a second set of teeth of an anvil feature.

In a further embodiment, a ramp is established at each location where a first set of teeth engage a second set of teeth.

In a further embodiment, a rotational component of a surgical impact driver adaptor is a second connector that is operably coupled to an anvil coupling.

In a further embodiment, a second connector of a surgical impact drive adaptor is a quick connect coupling.

In a further embodiment, an engagement assembly of a surgical impact driver adaptor includes an engagement device having a wave disk configuration.

An exemplary surgical method may include, inter alia, limiting a transfer of a rotational force from a powered surgical instrument to a surgical device until a sufficient axial force is applied to an impact driver adaptor from the powered surgical instrument during a surgical procedure.

In a further embodiment, a powered surgical instrument utilized in a surgical method is a surgical drill.

In a further embodiment, a surgical device utilized in a surgical method is a surgical drill bit or a surgical implant inserter.

FIG. 1 schematically illustrates a surgical system 10 that can be utilized for performing various surgical procedures. For example, the surgical system 10 may be used to prepare a bone for receiving a surgical implant, such as a suture anchor or an interference screw, and for implanting the surgical implant within the prepared bone. However, the surgical system 10 may be utilized to perform various other surgical procedures within the scope of this disclosure.

The surgical system 10 may include a powered surgical instrument 12 and a surgical device 14 that can be selectively driven (e.g., rotated) by the powered surgical instrument 12. In an embodiment, the powered surgical instrument 12 is a surgical drill that is configured to create axial and rotational forces for driving the surgical device 14 during a surgical procedure. The axial forces may create linear impact loads and the rotational forces may create torque loads for driving the surgical device 14.

Figure 2:
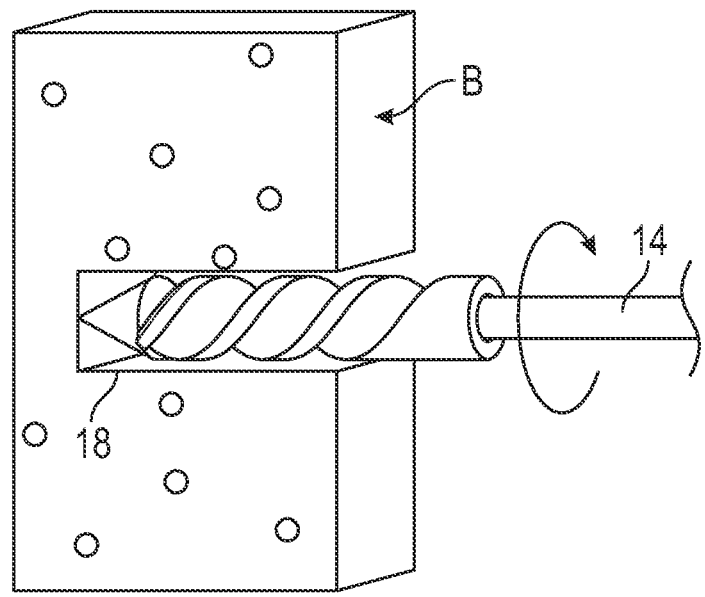
FIG. 2 schematically illustrates use of the surgical system of FIG. 1 for preparing a hole in a bone.

In an embodiment, the surgical device 14 is a drill bit that may be driven by the powered surgical instrument 12 in order to prepare a hole 18 in a bone B (see FIG. 2). The bone B could be any bone of the human musculoskeletal system.

Figure 3:
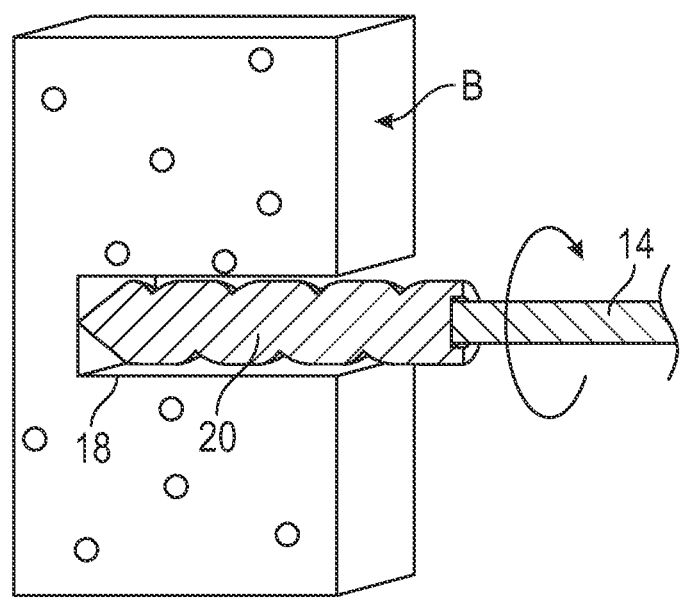
FIG. 3 schematically illustrates use of the surgical system of FIG. 1 for implanting a surgical implant into a prepared bone.

In another embodiment, the surgical device 14 is an implant inserter that may be driven by the powered surgical instrument 12 in order to implant a surgical implant 20 into the hole 18 formed in the bone B (see FIG. 3). The surgical implant 20 could be a suture anchor, an interference screw, or any other implantable surgical device.

The surgical system 10 may additionally include an impact driver adaptor 22. The impact driver adaptor 22 may be connected between the powered surgical instrument 12 and the surgical device 14 for transferring the axial and rotational forces created by the powered surgical instrument 12 to the surgical device 14. As discussed in greater detail below, the impact driver adaptor 22 may provide for a more controlled power transfer from the powered surgical instrument 12 to the surgical device 14 by limiting the torque applied to the surgical device 14 until an axial force of a sufficient threshold is applied from the powered surgical instrument 12 to the impact driver adaptor 22. Material fatigue and implant insertion site morbidity may be reduced by controlling power transfer from the powered surgical instrument 12 to the surgical device 14 in this way.

Figure 4:
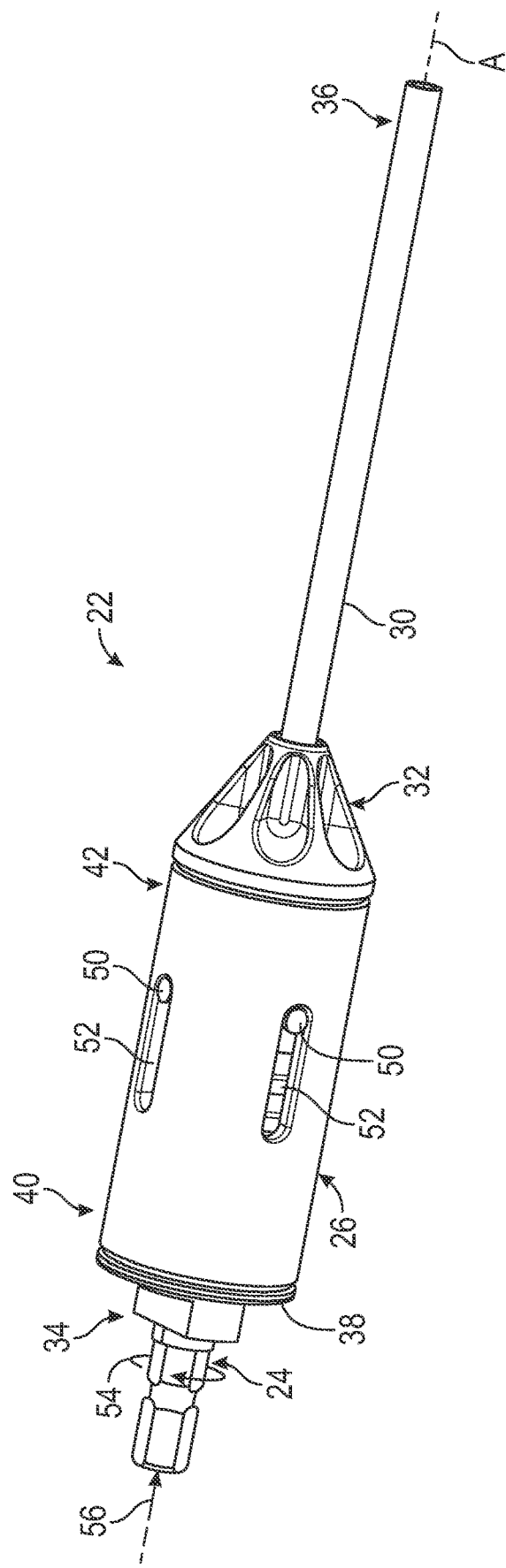
FIG. 4 is a perspective view of an exemplary impact driver adaptor.
Figure 5:
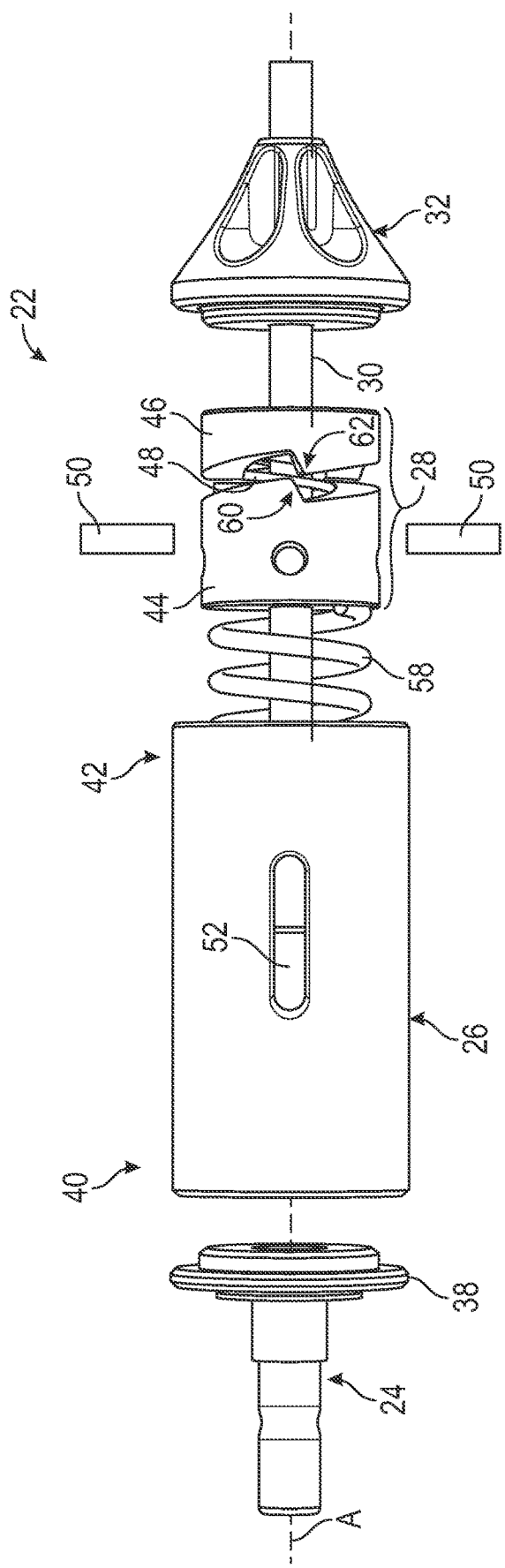
FIG. 5 is an exploded view of the impact drive adaptor of FIG. 4.
Figure 6:
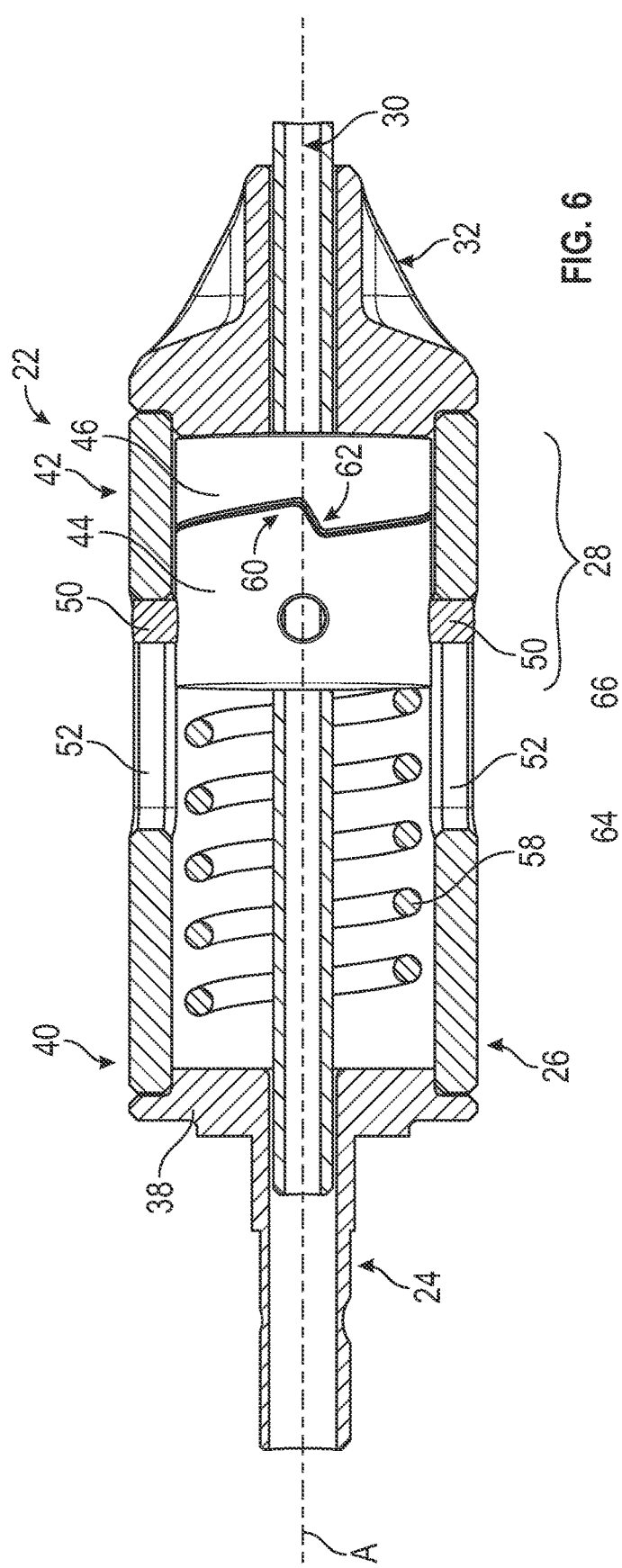
FIG. 6 is a partial cross-sectional view of the impact driver adaptor of FIG. 4.

FIGS. 4, 5, and 6 illustrate an exemplary impact driver adaptor 22 that may be utilized as part of the surgical system 10 of FIG. 1. The impact driver adaptor 22 may include, among various other components, a first connector 24, an outer sheath 26, an engagement assembly 28, a drive shaft 30, and a front cap 32. The impact driver adaptor 22 extends along a longitudinal axis A between a first or proximal portion 34 and a second or distal portion 36. The first connector 24 is located at the proximal portion 34 of the impact driver adaptor 22, and a distal end of the drive shaft 30 establish the distal portion 36 of the impact driver adaptor 22. The overall dimensions of the impact driver adaptor 22 are not intended to limit this disclosure.

The first connector 24 is configured for coupling the impact driver adaptor 22 to the powered surgical instrument 12. In an embodiment, the first connector 24 is configured as a Hudson connector. However, other types of connectors are alternatively contemplated within the scope of this disclosure for coupling the impact driver adaptor 22 to the powered surgical instrument 12.

The outer sheath 26 may include a cylindrical, tubular body that extends between a proximal end portion 40 and a distal end portion 42. A cap 38 of the first connector 24 may be fixedly secured (e.g., welded, bonded, etc.) to the proximal end portion 40 of the outer sheath 26, and the front cap 32 may be fixedly connected (e.g., welded, bonded, etc.) to the distal end portion 42 of the outer sheath 26. When the impact driver adaptor 22 is assembled, the engagement assembly 28 and portions of the drive shaft 30 are substantially housed within the outer sheath 26, and the front cap 32 axially constrains the engagement assembly 28 within the outer sheath 26.

The first connector 24, the outer sheath 26, the engagement assembly 28, the drive shaft 30, and the front cap 32 may be coaxial relative to one another, and at least a portion of the drive shaft 30 may be circumscribed by each of the first connector 24, the outer sheath 26, the engagement assembly 28, and the front cap 32. The drive shaft 30 may extend entirely through the outer sheath 26 and the front cap 32 to a location that is distally beyond the front cap 32 for connecting to the surgical device 14. Although not shown, the drive shaft 30 could include a second connector, such as a quick connect device, for example, for coupling the surgical device 14 to the impact driver adaptor 22.

The engagement assembly 28 may include a rear clutch cylinder 44, a front clutch cylinder 46, and a disengagement spring 48. The rear clutch cylinder 44 may include one or more pins 50 that may be received within corresponding slots 52 formed through the outer sheath 26. In an embodiment, four pins 50 and four corresponding slots 52 may be provided. However, other configurations are also possible. The pin(s) 50 may slide within the slot(s) 52 to guide axial translation of the rear clutch cylinder 44 along the longitudinal axis A during use of the impact driver adaptor 22 as part of the surgical system 10.

The drive shaft 30 may extend through the rear clutch cylinder 44 without being fixedly secured thereto. The rear clutch cylinder 44 is therefore free to rotate relative to the drive shaft 30. The front clutch cylinder 46 may be fixedly secured (e.g., welded or bonded) to the drive shaft 30.

The disengagement spring 48 (best shown in FIG. 5) may be received about a portion of the drive shaft 30 that is disposed between the rear clutch cylinder 44 and the front clutch cylinder 46. The disengagement spring 48 may extend between respective bearing surfaces of the rear clutch cylinder 44 and the front clutch cylinder 46 and is adapted to bias the rear clutch cylinder 44 in a direction away from the front clutch cylinder 46 (e.g., in the proximal direction) Therefore, in a default position of the impact driver adaptor 22, the drive shaft 30 is disengaged from a rotational force 54 applied from the powered surgical instrument 12 until an axial force 56 exceeding a predefined threshold is applied by the powered surgical instrument 12 for overcoming the biasing force of the disengagement spring 48. Once the biasing force is overcome by the axial force 56, the rear clutch cylinder 44 may engage the front clutch cylinder 46 to begin rotating the drive shaft 30.

In an embodiment, the rotational force 54 is applied circumferentially about the longitudinal axis A, and the axial force 56 is applied in a direction along the longitudinal axis A (see FIG. 4). The axial force 56 may alternatively be referred to as a normal force or a linear force. The axial force 56 may create a linear impact load for driving the surgical device 14, and the rotational force 54 may create a torque load for driving the surgical device 14.

The impact driver adaptor 22 may additionally include a spring 58. The spring 58 is a separate component from the disengagement spring 48 and may be housed within the outer sheath 26. The spring 58 may be positioned between the cap 38 and the rear clutch cylinder 44, for example. The spring 58 may function as a dampening mechanism for smoothing the axial force 56 that is applied to the impact driver adaptor 22 from the powered surgical instrument 12. Dampening linear impact loads in this manner provides the user with more control during operation, thereby reducing implant insertion site morbidity.

In an embodiment, the disengagement spring 48 and the spring 58 are both coil springs. However, other types of springs may also be suitable and are further contemplated within the scope of this disclosure.

During uses of the impact driver adaptor 22, the powered surgical instrument 12 may apply the rotational force 54 to the first connector 24, thereby causing the outer sheath 26 and the rear clutch cylinder 44 to begin rotating about the longitudinal axis A. The front clutch cylinder 46 and the drive shaft 30 remain stationary at this stage of the operation.

As operation continues, the powered surgical instrument 12 may begin applying the axial force 56 to the impact drive adaptor 22. Once the axial force 56 exceeds a predefined threshold, the biasing force of the disengagement spring 48 is overcome, thereby allowing the rear clutch cylinder 44 to engage the front clutch cylinder 46 and thus begin rotating the drive shaft 30. The rotational torque of the drive shaft 30 may then begin driving the surgical device 14.

The magnitude of the axial force 56 necessary for overcoming the predefined threshold may vary depending on the desired application and could be between about 2 pounds (lbs.) and about 40 pounds (lbs.). In this disclosure, the term "about" means that the expressed quantities or ranges need not be exact but may be approximated and/or larger or smaller, reflecting acceptable tolerances, conversion factors, measurement error, etc. For example, the axial force 56 could be about 2 lbs. when the surgical device 14 is a drill bit, could be about 10 lbs. when the surgical device 14 is a suture anchor inserter for inserting a PEEK/metallic suture anchor, or could be between about 20 lbs. and about 40 lbs. when the surgical device 14 is a suture anchor inserter for inserting a biocompo site suture anchor.

The magnitude of the axial force 56 may further depend on the drive mechanism used to connect the drive shaft 30 to the surgical device 14. For example, hexalobe drive mechanisms may provide a relatively low amount of axial force 56, hex drive mechanisms may provide a relatively large amount of axial force 56, and torx drive mechanisms may provide an amount of axial force 56 that is between that provided by the hexalobe and hex mechanisms.

Figure 7:
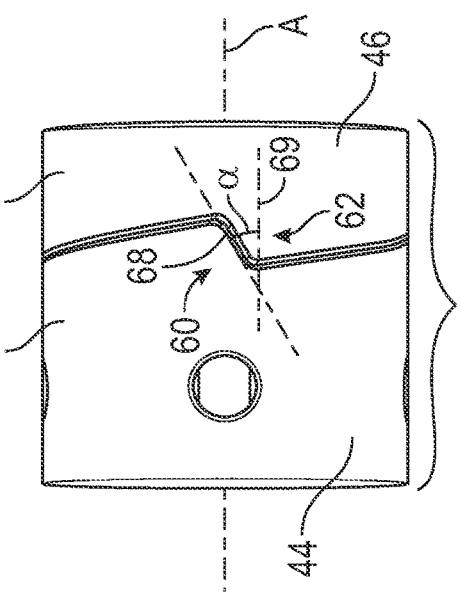
FIG. 7 illustrates exemplary mating features of an engagement assembly of the impact driver adaptor of FIG. 4.

Referring now primarily to FIGS. 5-7, the engagement assembly 28 of the impact driver adaptor 22 may include mating features that allow the rear clutch cylinder 44 to engage the front clutch cylinder 46 for rotating the drive shaft 30. For example, the rear clutch cylinder 44 may include a first set of teeth 60 that are dimensioned to engage and mesh with a second set of teeth 62 of the front clutch cylinder 46 for enabling rotation of the drive shaft 30. The first set of teeth 60 may be provided at an outer cylindrical surface 64 of the rear clutch cylinder 44, and the second set of teeth 62 may be provided at an outer cylindrical surface 66 of the front clutch cylinder 46 (see, e.g., FIG. 7).

Each set of teeth 60, 62 may include two or more teeth that are circumferentially spaced apart from one another along one of the outer cylindrical surfaces 64, 66. The total number of teeth provide in each set 60, 62 may depend on various factors, including but not limited to the desired torque limit of the impact driver adaptor 22.

The first and second set of teeth 60, 62 may each include a sawtooth-like geometry. However, other geometries, such as rectangular profiles, for example, may alternatively be utilized.

As best illustrated in FIG. 7, a ramp 68 may be established at each location where the first set of teeth 60 engage the second set of teeth 62. Each ramp 68 may extend at an angle α relative to an axis 69 that is parallel to the longitudinal axis A. In an embodiment, the angle is α between about 2 degrees and about 60 degrees. In general, the lower the angle α of the ramp 68, the higher the amount of torque that can be transferred by the impact driver adaptor 22. Therefore, the angle α of the ramp 68 is another factor that can vary depending on design specific parameters such as the desired torque limit of the impact driver adaptor 22.

The actual amount of the angle α may vary depending on the amount of rotary impact that is desired for a specific application. For example, the angle α could be about 60 degrees (less rotation relative to axial impact) when drilling to create bone tunnels, could be about 10 degrees when inserting suture anchors of tougher materials (e.g., PEEK), could be about 2 degrees when inserting metallic suture anchors or interference screws, or could be about 30 degrees when inserting biocomposite suture anchors.

The rotary impact transferred to the surgical device may further be controlled based on the drive mechanism used to connect the drive shaft 30 to the surgical device 14. For example, hexalobe drive mechanisms may provide a relatively high amount of rotary impact, hex drive mechanisms may provide a relatively low amount of rotary impact, and torx drive mechanisms may provide an amount of rotary impact that is between that provided by the hexalobe and hex mechanisms.

Figure 8:
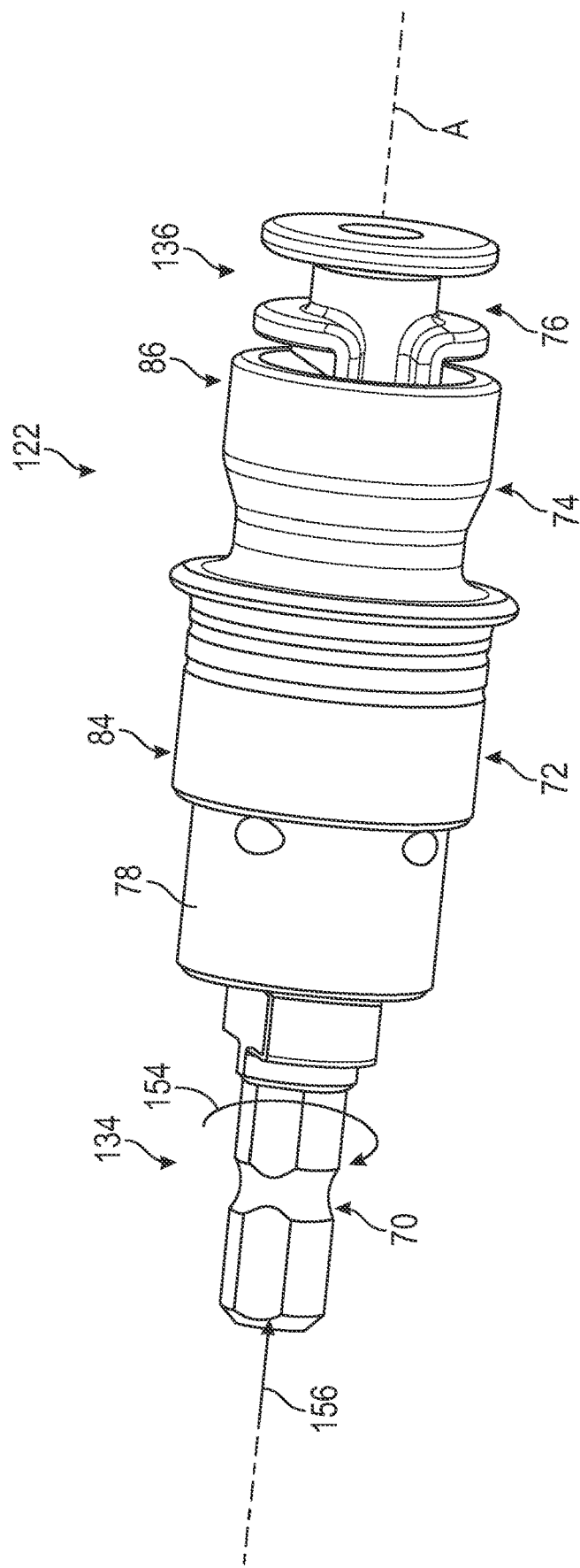
FIG. 8 is a perspective view of another exemplary impact driver adaptor.
Figure 9:
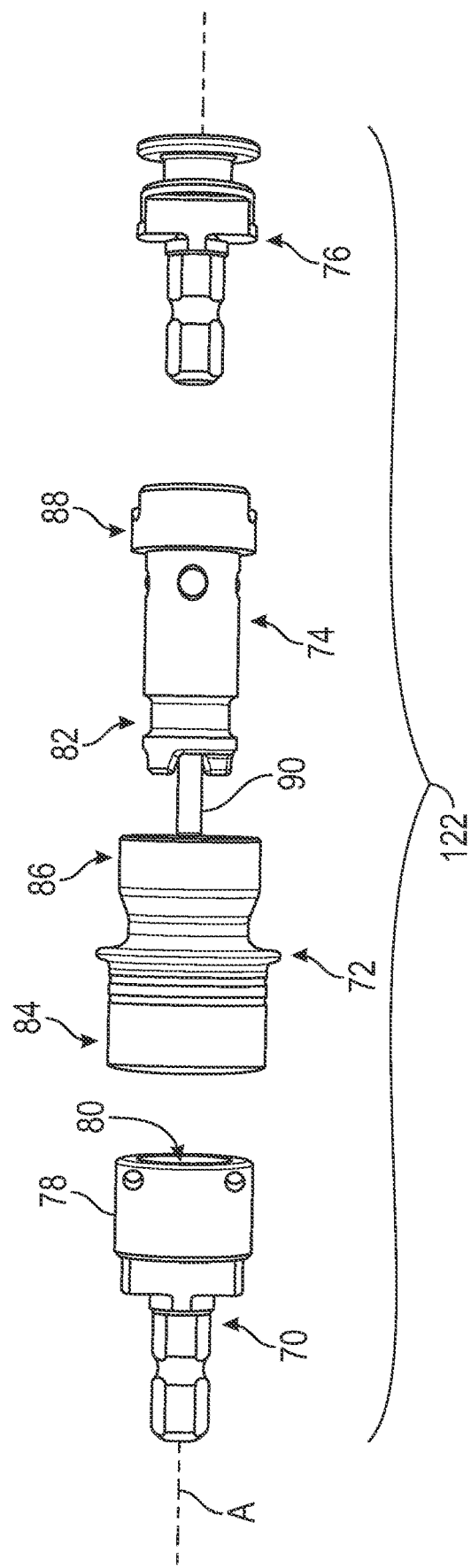
FIG. 9 is an exploded view of the impact drive adaptor of FIG. 8.
Figure 10:
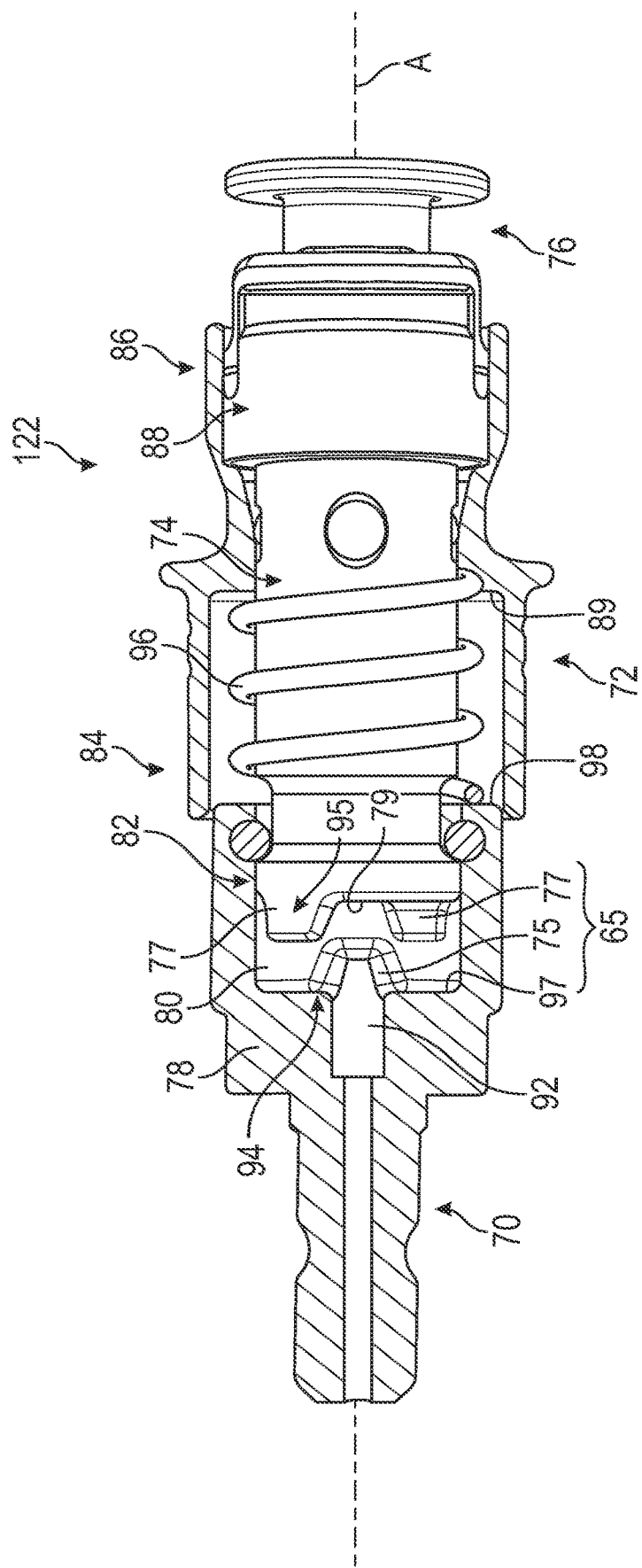
FIG. 10 is a partial cross-sectional view of the impact driver adaptor of FIG. 8.

FIGS. 8, 9, and 10 illustrate another exemplary impact driver adaptor 122 that may be used as part of the surgical system 10 of FIG. 1. The design of the impact driver adaptor 122 is structurally different from that of the impact driver adaptor 22. Among other differences, the impact driver adaptor 122 provides a smaller longitudinal footprint compared to the impact driver adaptor 22. Nevertheless, like the impact driver adaptor 22, the impact driver adaptor 122 is configured to function to limit the torque applied to the surgical device 14 until an axial force of a sufficient magnitude is applied from the powered surgical instrument 12 to the impact driver adaptor 122.

The impact driver adaptor 122 may include, among various other components, a first connector 70, an outer locking sheath 72, an anvil coupling 74, and a second connector 76. The impact driver adaptor 122 extends along a longitudinal axis A between a first or proximal portion 134 and a second or distal portion 136. The first connector 70 is located at the proximal portion 134 of the impact driver adaptor 122, and the second connector 76 is located at the distal portion 136 of the impact driver adaptor 122. The overall dimensions of the impact driver adaptor 122 are not intended to limit this disclosure. The first connector 70, the outer locking sheath 72, the anvil coupling 74, and the second connector 76 may be arranged in a coaxial relationship relative to one another along the longitudinal axis A.

The first connector 70 is configured for coupling the impact driver adaptor 122 to the powered surgical instrument 12. In an embodiment, the first connector 70 is configured as a Hudson connector. However, other types of connectors are alternatively contemplated within the scope of this disclosure for coupling the impact driver adaptor 122 to the powered surgical instrument 12.

The second connector 76 is configured to coupling the surgical device 14 to the impact driver adaptor 122. In an embodiment, the second connector 76 is configured as a quick connect coupling. However, other types of connectors are alternatively contemplated within the scope of this disclosure for coupling the surgical device 14 to the impact driver adaptor 122.

The first connector 70 may include a boss 78 having an inner bore 80. The inner bore 80 may be sized to accommodate a proximal portion 82 of the anvil coupling 74.

The outer locking sheath 72 may include a tapered cylindrical tubular body that extends between a proximal end portion 84 and a distal end portion 86. The proximal end portion 84 is configured to interface with the boss 78 of the first connector 70, and the distal end portion 86 is configured to interface with both a distal portion 88 of the anvil coupling 74 and the second connector 76. In an embodiment, the proximal end portion 84 of the outer locking sheath 72 is movably secured relative to the boss 78 of the first connector 70. When the impact driver adaptor 122 is assembled, the anvil coupling 74 is substantially housed within the boss 78 of the first connector and the outer locking sheath 72.

A shaft 90 (see FIG. 9) may extend from the proximal portion 82 of the anvil coupling 74. The shaft 90 may be received within a passage 92 (see FIG. 10) of the first connector 70. The passage 92 may connect to the inner bore 80.

A hammer feature 94 may be provided by the boss 78 of the first connector 70. The hammer feature 94 is configured to interface with a corresponding anvil feature 95 of the proximal portion 82 of the anvil coupling 74 for establishing an engagement assembly 65 (see FIGS. 10-11) of the impact driver adaptor 122.

A disengagement spring 96 (see FIG. 10) may be housed within the outer locking sleeve 72. The disengagement spring 96 may be positioned between a distal flange 98 of the boss 78 and an inner diameter flange 89 of the outer locking sleeve 72. The disengagement spring 96 may bias the anvil coupling 74 in a direction away from the hammer feature 94 (e.g., distally). Therefore, in a default position of the impact driver adaptor 122, the anvil coupling 74 (and thus the second connector 76) is disengaged from a rotational force 154 applied from the powered surgical instrument 12 to the first connector 70 until a sufficient axial force 156 is applied by the powered surgical instrument 12 for overcoming the biasing force of the disengagement spring 96. Once the biasing force is overcome by the axial force 156, the hammer feature 94 may engage the anvil feature 95 and begin rotating the anvil coupling 74 (and thus the second connector 76 and any surgical device connected thereto).

In an embodiment, as best shown in FIG. 8, the rotational force 154 is applied circumferentially about the longitudinal axis A, and the axial force 156 is applied in a direction along the longitudinal axis A. The axial force 156 may create a linear impact load for driving the surgical device 14, and the rotational force 154 may create a torque load for driving the surgical device 14.

During use of the impact driver adaptor 122, the powered surgical instrument 12 may apply the rotational force 154 to the first connector 70, thereby rotating the first connector 70 about the longitudinal axis A relative to the other subcomponents of the impact driver adaptor 122. The outer locking sheath 72, the anvil coupling 74, and the second connector 76 each remain stationary at this stage of the operation.

As operation continues, the powered surgical instrument 12 will begin applying the axial force 156 to the impact drive adaptor 122. Once the axial force 156 exceeds a predefined threshold, the biasing force of the disengagement spring 96 is overcome, thereby allowing the anvil coupling 74 to travel proximally and permit the anvil feature 95 and the hammer feature 94 to engage one another and begin rotating the anvil coupling 74. The rotational torque from the powered surgical instrument 12 may then be transferred through the anvil coupling 74 and the second connector 76 for driving the surgical device 14.

Figure 11:
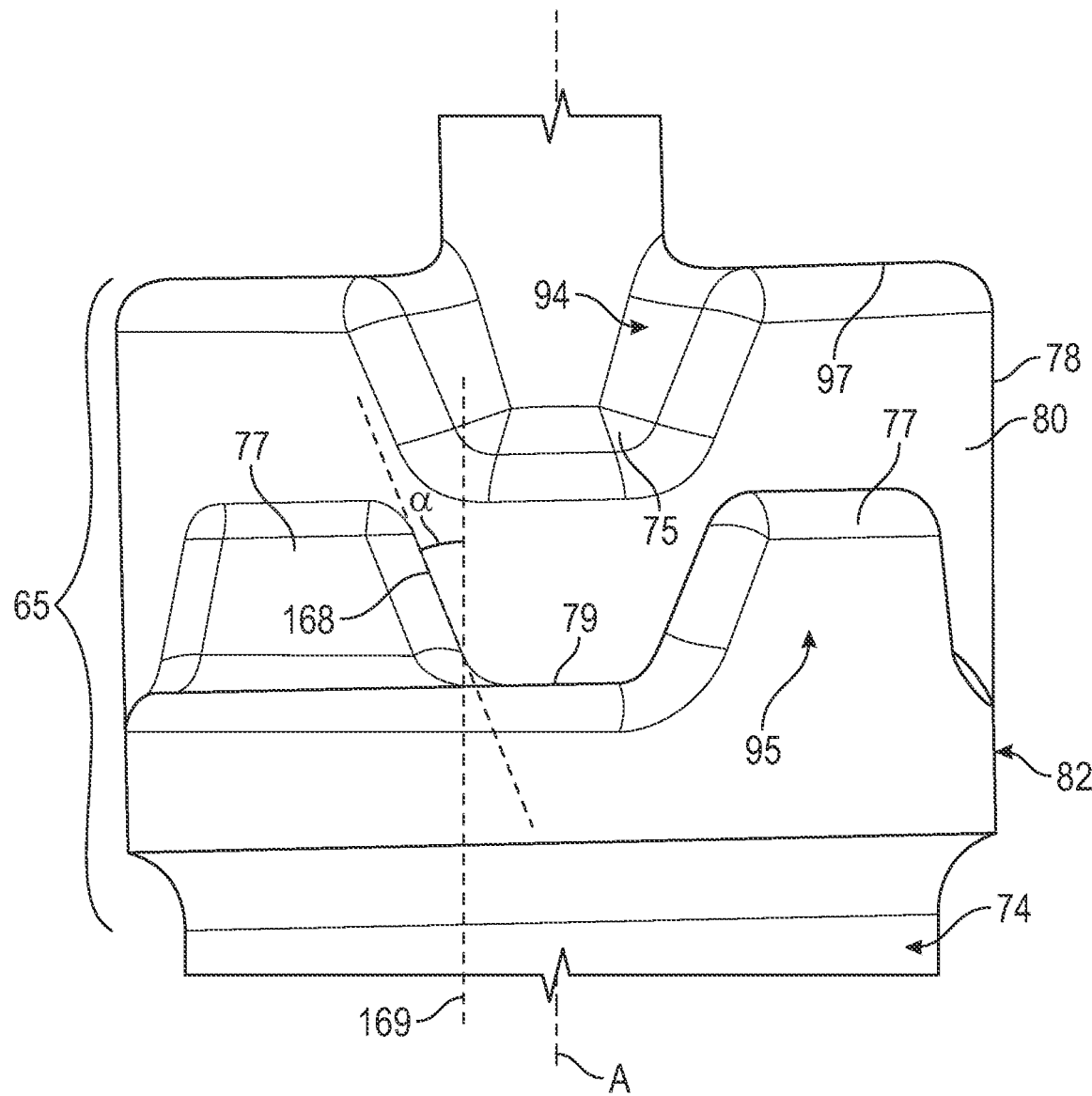
FIG. 11 illustrates exemplary mating features of an engagement assembly of the impact driver adaptor of FIG. 8.

Referring now primarily to FIGS. 10-11, the hammer feature 94 and the anvil feature 95 may each include mating features for allowing the first connector 70 and the anvil coupling 74 to operably engage one another. For example, the hammer feature 94 may include a first set of teeth 75 that are dimensioned to engage and mesh with a second set of teeth 77 of the anvil feature 95 for enabling rotation of the anvil coupling 74. The first set of teeth 75 may protrude from a floor 97 of the boss 78, and the second set of teeth 77 may protrude from a planar face 79 of the proximal portion 82 of the anvil coupling 74.

Each set of teeth 75, 77 may include two or more teeth that are circumferentially spaced apart from one another. The teeth of the first set of teeth 75 may be circumferentially spaced from one another along a planar face established by the floor 97, and the teeth of the second set of teeth 77 may be circumferentially spaced from one another about the planar face 79. The total number of teeth provided in each set 75, 77 may depend on various factors, including but not limited to the desired torque limit of the impact driver adaptor 122.

A ramp 168 is established at each location where the first set of teeth 75 engage the second set of teeth 77. Each ramp 168 may extend at an angle α relative to an axis 169 that is substantially parallel to the longitudinal axis A. In an embodiment, the angle is α between about 2 degrees and about 60 degrees. In general, the lower the angle α of the ramp 168, the higher the amount of torque that can be transferred by the impact driver adaptor 122. Therefore, the angle α of the ramp 168 is another factor that can vary depending on design specific parameters such as the desired torque limit of the impact driver adaptor 122.

Figure 12:
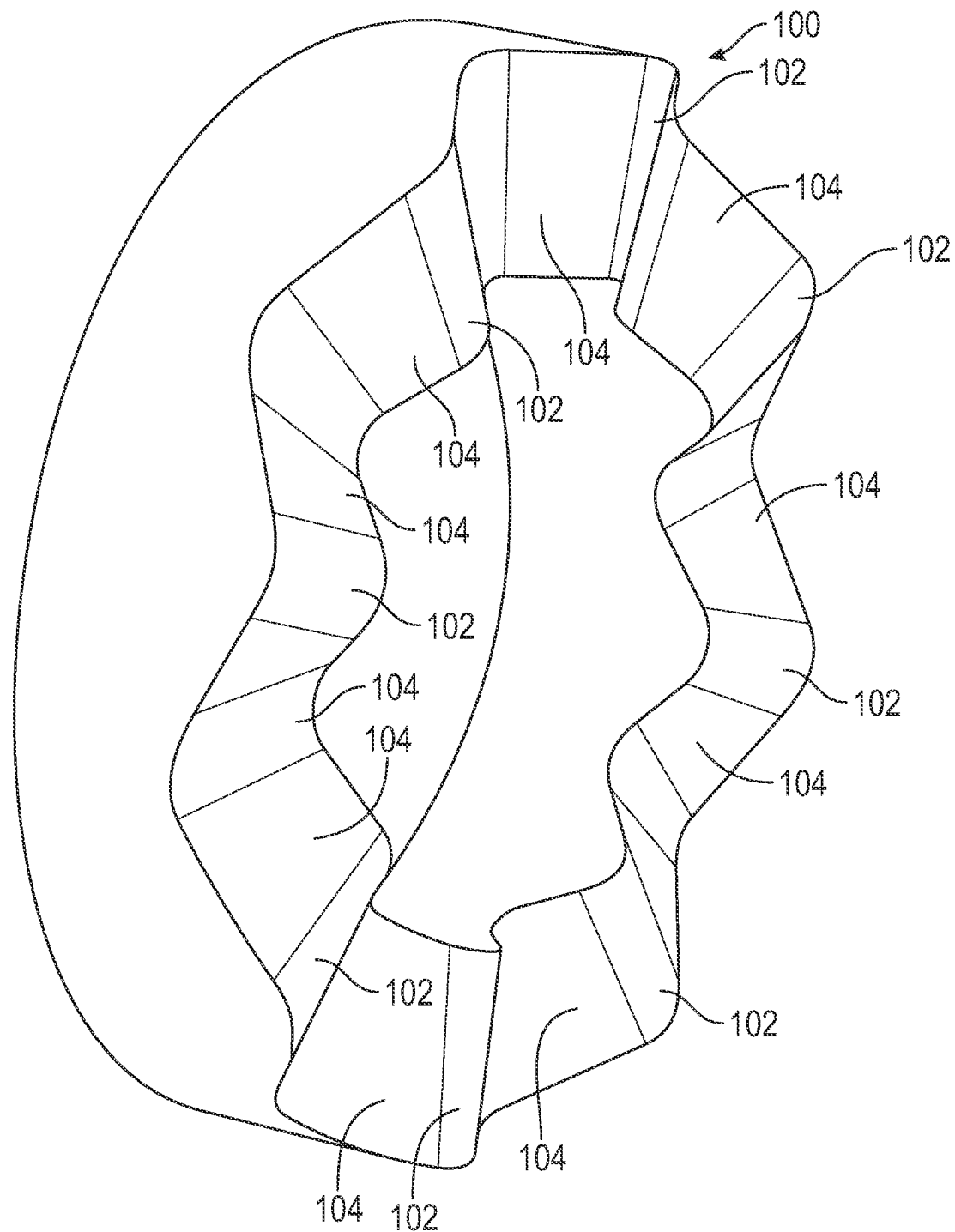
FIG. 12 illustrates an exemplary engagement device that can be incorporated into an engagement assembly of an impact driver adaptor.

FIG. 12 illustrates an exemplary engagement device 100. The engagement device 100 could be incorporated as part of the engagement assembly 28 of the impact driver adaptor 22 or as part of the engagement assembly 65 of the impact driver adaptor 122 for controlling the transfer of torque loads from a powered surgical instrument to a driven surgical device.

In an embodiment, the engagement device 100 includes a wave disk design having a plurality of engageable features 102 (e.g., teeth). The engageable features 102 provide ramped engagement surfaces 104 adapted for engaging corresponding ramped surfaces of a second engagement device for transferring torque. The design of the engagement device 100 allows for a relatively low amount of torque to be applied relative to axial forces. The design of the engagement device 100 may be particularly suitable for driving certain types of drill bits, for example.

The impact driver adaptors of this disclosure advantageously provide ramped engagement of rotary loads when drilling or inserting surgical implants. The unique drive/engagement mechanisms discussed herein allow for disengagement of the driven surgical device until a desired axial load is achieved, thereby removing certain failure modes and material constraints. Further, the exemplary impact driver adaptors discussed herein exhibit self-dampening designs that absorb impact loads in a manner than can reduce implant insertion site morbidity.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical impact driver adaptor, comprising:
   a first connector adapted to receive a rotational force;
   a second connector;
   an outer locking sleeve including a proximal end portion configured to interface with a boss of the first connector and a distal end portion configured to interface with the second connector;
   an anvil coupling including a proximal end portion received within an inner bore of the boss of the first connector,
   wherein the anvil coupling is substantially housed within the boss and the outer locking sleeve;
   the boss of the first connector providing a hammer feature;
   the proximal end portion of the anvil coupling providing an anvil feature configured to mate with and engage the hammer feature; and
   a disengagement spring configured to bias the anvil feature and the hammer feature apart, thereby disengaging the second connector from receiving the rotational force until an axial force that exceeds a predefined threshold is applied to the first connector.

2. The surgical impact driver adaptor as recited in claim 1, wherein the hammer feature includes a first set of teeth that are configured to engage and mesh with a second set of teeth of the anvil feature.

3. The surgical impact driver adaptor as recited in claim 2, wherein the first set of teeth protrude from a floor of the boss of the first connector, and the second set of teeth protrude from a planar face of the proximal end portion of the anvil coupling.

4. The surgical impact driver adaptor as recited in claim 3, wherein the first set of teeth includes at least two teeth that are circumferentially spaced from one another along a planar face established by the floor, and the second set of teeth includes at least two teeth that are circumferentially spaced from one another along the planar face of the proximal end portion.

5. The surgical impact driver adaptor as recited in claim 2, wherein a ramp is established at each location where the first set of teeth engage the second set of teeth, and further wherein the ramp extends at an angle relative to an axis that is substantially parallel to a longitudinal axis of the surgical impact driver adaptor.

6. The surgical impact driver adaptor as recited in claim 5, comprising a drill bit coupled to the surgical impact driver adaptor by the second connector, and wherein the angle of the ramp is about 60 degrees.

7. The surgical impact driver adaptor as recited in claim 5, comprising an implant inserter coupled to the surgical impact driver adaptor by the second connector, wherein the angle of the ramp is about 2 degrees, about 10 degrees, or about 3 degrees.

8. The surgical impact driver adaptor as recited in claim 5, wherein the angle of the ramp is between about 2 degrees and about 60 degrees.

9. A surgical impact driver adaptor, comprising:
   a first connector adapted to receive a rotational force;
   a rotational component operably coupled to the first connector; and
   an engagement assembly configured to disengage the rotational component from receiving the rotational force until an axial force that exceeds a predefined threshold is applied to the first connector,
   wherein the engagement assembly includes a hammer feature provided by the first connector, an anvil feature provided by an anvil coupling, and a disengagement spring that is configured to bias the hammer feature and the anvil feature apart until the axial force exceeds the predefined threshold, wherein the hammer feature includes a first set of teeth that are configured to engage and mesh with a second set of teeth of the anvil feature.

10. The surgical impact driver adaptor as recited in claim 9, wherein the first connector is configured to receive the rotational force from a powered surgical instrument.

11. The surgical impact driver adaptor as recited in claim 9, wherein the rotational component is configured to connect to a surgical device.

12. The surgical impact driver adaptor as recited in claim 11, wherein the rotational component is a drive shaft.

13. The surgical impact driver adaptor as recited in claim 11, wherein the rotational component is a second connector.

14. The surgical impact driver adaptor as recited in claim 9, wherein a ramp is established at each location where the first set of teeth engage the second set of teeth.

15. The surgical impact driver adaptor as recited in claim 9, wherein the rotational component is a second connector that is operably coupled to the anvil coupling.

16. The surgical impact driver adaptor as recited in claim 15, wherein the second connector is a quick connect coupling.

17. The surgical impact driver adaptor as recited in claim 9, wherein the engagement assembly includes an engagement device that includes a wave disk configuration.

18. A surgical impact driver adaptor, comprising:
a first connector adapted to receive a rotational force;
a rotational component operably coupled to the first connector;
an engagement assembly configured to disengage the rotational component from receiving the rotational force until an axial force that exceeds a predefined threshold is applied to the first connector,
wherein the engagement assembly includes a rear clutch cylinder, a front clutch cylinder, and a disengagement spring that is configured to bias the rear clutch cylinder and the front clutch cylinder apart until the axial force exceeds the predefined threshold; and
a spring arranged between a cap of the first connector and the rear clutch cylinder, wherein the spring is configured to dampen linear impact loads created by the axial force.

19. The surgical impact driver adaptor as recited in claim 18, wherein the rear clutch cylinder includes a first set of teeth that are configured to engage and mesh with a second set of teeth of the front clutch cylinder.

20. The surgical impact driver adaptor as recited in claim 19, wherein a ramp is established at each location where the first set of teeth engage the second set of teeth.

* * * * *